United States Patent [19]
Penninger et al.

[11] Patent Number: 5,663,439
[45] Date of Patent: Sep. 2, 1997

[54] PROCESS FOR THE PREPARATION OF TOLUIDINES

[75] Inventors: Stefan Penninger, Pulheim; Peter Heitkämper, Dormagen, both of Germany

[73] Assignee: Bayer Aktiengesellschaft, Leverkusen, Germany

[21] Appl. No.: 689,861

[22] Filed: Aug. 15, 1996

[30] Foreign Application Priority Data

Aug. 24, 1995 [DE] Germany .................... 19531149.3

[51] Int. Cl.$^6$ .................................. C07C 209/68
[52] U.S. Cl. .............................. 564/305; 564/437
[58] Field of Search ...................... 564/305; 585/400, 585/469

*Primary Examiner*—Brian M. Burn
*Attorney, Agent, or Firm*—Joseph C. Gil; N. Denise Brown

[57] ABSTRACT

The present invention relates to an improved process for the preparation of toluidines. This process comprises the reductive deamination of 2,3-diaminotoluenes and/or 3,4-diaminotoluenes in the presence of one or more iron oxide catalyst.

4 Claims, No Drawings

PROCESS FOR THE PREPARATION OF TOLUIDINES

BACKGROUND OF THE INVENTION

The present invention relates to an improved process for the preparation of toluidines by the reductive deamination of 2,3-diaminotoluene, 3,4-diaminotoluene, or mixtures thereof.

2,3- and 3,4-diaminotoluene are constituents of toluylenediamine, which is produced on a large scale. In the conventional further processing of toluylenediamine to toluylene diisocyanate, 2,3- and 3,4-diaminotoluene, which are collectively referred to hereafter as o-diaminotoluene, would interfere and are therefore separated off beforehand, generally by distillation. This o-diaminotoluene which has been separated off is used for the preparation of various chemical products. However, the amount of o-diaminotoluene obtained is frequently greater than that which is required for these applications.

The object of the present invention is, therefore, to utilize excess o-diaminotoluene in an economically and ecologically sensible manner.

It is known that o-diaminotoluene can be catalytically hydrogenated to form toluidines. This hydrogenation is accompanied by the elimination and release of ammonia and is therefore referred to as reductive deamination. Since both ammonia and, particularly, toluidines are valuable key chemicals, the reductive deamination of o-diaminotoluene is a very sensible reaction in terms of the object of the present invention.

U.S. Pat. No. 3,532,754 describes a process for the preparation of o- and m-toluidine by the reductive deamination of o-diaminotoluene. That process comprises reacting o-diaminotoluene with hydrogen under elevated pressure at temperatures of 200° to 250° C., in the presence of supported catalysts based on cobalt oxide. However, this process suffers from serious disadvantages.

This process produces inadequate yields of toluidine. It is evident from Examples 1 and 4 of the '754 patent that the total yield of toluidine after a reaction time of 4.5 or 7 hours at a reaction temperature of 225° C. is only 52 or 46%, respectively, of theory, based on the starting o-diaminotoluene. This is partly due to the fact that the conversion of the starting o-diaminotoluene is low. For example, the conversion in Example 1 of the patent after a reaction time of 4.5 hours at 225° C. is only 64%.

For a reaction time of 5.25 hours at 225° C., Example 3 of the patent presents numerical results which suggest that the conversion of the starting o-diaminotoluene is less than 20%. However, as a reaction temperature of 225° C. is exactly within the range 215° to 235° C., which is disclosed therein as the preferred range, the cobalt catalysts described in the patent have to be regarded as unsuitable for this reaction since they only produce inadequate conversions of the starting o-diaminotoluene.

On the other hand, U.S. Pat. No. 3,532,754 (at column 2, lines 23 to 29) discloses that the reductive deamination of o-diaminotoluene at temperatures of about 250° C., in the presence of the cobalt catalysts, results in the formation of toluene, i.e., reductive deamination and hence decomposition of the desired reaction products, and that, at even higher reaction temperatures, ring hydrogenations also take place to form methylcyclohexylamine and methylcyclohexane. This statement is further confirmed by the examples of this patent.

Similar to toluene, methylcyclohexylamine and methylcyclohexane are comparatively worthless products, and must be removed by costly procedures. The formation of these by-products in the reductive deamination should be suppressed as far as possible. According to the '754 patent, this is achieved by choosing appropriately low reaction temperatures. As explained above, however, uneconomically low conversions have to be accepted as a consequence of these low reaction temperatures.

A further disadvantage of said process is that it yields practically no p-toluidine, if any. As shown by Example 1 and claims 7 and 8 of the '754 patent, the reaction of o-diaminotoluene by the described process results only in o-toluidine and m-toluidine, with only trace quantities of p-toluidine being detectable in the reaction mixtures. From a statistical viewpoint, this circumstance is surprising. It suggests that the described cobalt catalysts have a selective action in the reaction, and thereby prevent the formation of p-toluidine. However, it is precisely p-toluidine which is a valuable key chemical. Thus, the probable selectivity of the cobalt catalysts in the reductive deamination of o-diaminotoluene results in a considerable disadvantage.

Finally, the process of the '754 patent also suffers from the disadvantage that the reactions demand high concentrations of cobalt catalysts. According to the patent, the preferred concentrations are 30 to 60 parts by weight of catalyst, based on 100 parts by weight of starting o-diaminotoluene. These high concentrations inevitably result in a marked deterioration in the space-time yields. In particular, they require considerable technical effort, particularly in the working-up of the reaction mixtures, for example, in the separation of the catalysts by filtration or in the separation of the mixtures by distillation.

U.S. Pat. No. 4,329,501 describes another process for the preparation of toluidines by the reaction of 2,3- and 3,4-diaminotoluene with hydrogen under elevated pressure. This process is characterized in that cobalt metal is used as the catalyst, and the reactions are carried out in the presence of water as solvent.

In the '501 patent, the described experimental examples are intended to verify the mode of action of the claimed process. The results of these examples are collated in a table. However, it is unclear which of the described examples are to be regarded as being representative of the process described by the '501 patent, and which are comparative examples. In particular, the results of the described experiments are only given in the form of relative contents, determined by gas chromatography (area %), of the reaction mixtures from which the catalyst has been removed by filtration, without indicating their absolute amounts or, where appropriate, their water content. Also, since there is no data on the amounts of recovered starting material, this table gives no information either on the conversions of starting o-diaminotoluene achieved or on the yields of desired toluidine obtained. Thus, these examples are of little use in assessing the claimed process.

This table of the '501 patent does, however, show that the times of the described reactions are about 10 to 20 hours, i.e. relatively long. This is not surprising since o-diaminotoluene is used in solution in a solvent and, in accordance with the law of mass action, reacts more slowly than in undiluted form.

Therefore, the object of the present invention is to provide an improved process for the preparation of toluidines by the reductive deamination of 2,3-diaminotoluene and 3,4-diaminotoluene. This improved process should result in minimal quantities of by-products, and, simultaneously, high conversion rates of the starting diaminotoluene.

DESCRIPTION OF THE INVENTION

The present invention provides a process for the preparation of toluidines by 1) reacting a) 2,3-diaminotoluene and/or 3,4-diaminotoluene with b) hydrogen, in the presence of c) a catalyst comprising at least one iron oxide, wherein said reaction is carried out under elevated pressure and at temperatures in the range of about 260° to 350° C.

Chemically pure 2,3-diaminotoluene or 3,4-diaminotoluene or mixtures of these two compounds can be used as reactants in the process according to the invention. It is also possible, however, to use technical-grade mixtures of 2,3-diaminotoluene and 3,4-diaminotoluene, such as those obtained, for example, from the separation of o-diaminotoluene from technical-grade toluylenediamine by distillation.

The reactions according to the present invention are preferably carried out in the absence of solvents. However, the concomitant use of inert solvents in the process of the present invention is not excluded in principle, if the particular circumstances demand it.

The process of the present invention can be carried out either batchwise or continuously.

In accordance with the present invention, the following iron oxides are suitable examples of catalysts to be used: FeO (wuestite), $Fe_2O_3$, $Fe_3O_4$ and hydrated oxides of divalent and/or trivalent iron such as, for example, rust. The iron oxides can be used either individually or in a mixture with one another.

The amount of iron oxide catalysts to be used in the present process is typically about 1 to 12 parts by weight, preferably 3 to 9 parts by weight, based on 100 parts by weight of diaminotoluene to be reacted.

In the process of the present invention, the catalysts are used in a form having a high surface area. For example, the catalysts for the present process can be mixed in finely crystalline or powdered form into the o-diaminotoluene which is to be reacted. It is also possible, however, to sinter the finely divided iron oxides on a support having a high surface area and to use this support, treated with iron oxide, as a fixed bed catalyst. Examples of supports which are suitable for this process include pumice, siliceous earth, silica gel, aluminosilicates and aluminium oxide.

The reaction temperatures for the process according to the invention are in the range of about 260° to 350° C., preferably about 280° to 330° C.

The process is conventionally carried out at a hydrogen pressure of about 200 to 400 bar, preferably about 250 to 350 bar.

The reaction times of the process of the invention are greatly dependent on the selected reaction temperature and the quantity of catalyst used. The reaction time which is favorable for the particular conditions can easily be determined by means of appropriate preliminary experiments. It is typically from about 0.5 to 10 hours. The reaction times are conveniently chosen so that virtually no by-products are formed in the reactions. In order to avoid secondary reactions, it may be advantageous to accept slightly smaller conversions by shortening the reaction times accordingly, as is shown in the examples.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

A series of 7 identical reactions according to the present invention were carried out in which only the reaction time was varied. Reaction times for each example are set forth in Table 1. The results of these reactions are also set forth in Table 1.

General Procedure Followed in Examples 1 to 7

A mixture of 146 g of 2,3-diaminotoluene, 254 g of 3,4-diaminotoluene and 25 g of powdered $Fe_2O_3$ were placed in a 0.7 l autoclave, and stirred. The autoclave was flushed with nitrogen. Then, the mixture was hydrogenated at 300° C. and a hydrogen pressure of 260 bar. When the chosen reaction time had elapsed, the pressure in the autoclave was released, and the ammonia formed as a gas escaped. The reaction mixture was removed and filtered on a pressure suction filter to separate off the catalyst. Quantitative analysis was performed by gas chromatography. Authentic samples of the individual components were used as internal standards for calibration purposes.

TABLE 1

| | Results of Examples 1 to 7 | | | | | | |
|---|---|---|---|---|---|---|---|
| Example | 1 | 2 | 3 | 4 | 5 | 6 | 7 |
| Reaction time (h) | 1.0 | 2.0 | 3.0 | 4.0 | 5.0 | 6.0 | 11.0 |
| Reaction mixture (catalyst-free) | | | | | | | |
| Weight (g)[a] | 365 | 362 | 360 | 359 | 359 | 358 | 350 |
| Composition (wt. %) | | | | | | | |
| Toluene | 0.33 | 0.35 | 0.42 | 0.41 | 0.34 | 0.50 | 7.9 |
| Methylcyclohexane | 0.00 | 0.00 | 0.00 | 0.00 | 0.00 | 0.00 | 0.00 |
| Methylcyclohexylamine | 0.00 | 0.00 | 0.00 | 0.00 | 0.10 | 0.10 | 0.63 |
| o-Toluidine | 10.7 | 13.0 | 15.8 | 17.0 | 17.6 | 18.5 | 20.8 |
| m-Toluidine | 34.0 | 36.7 | 37.2 | 37.6 | 37.9 | 38.0 | 37.5 |
| p-Toluidine | 23.7 | 25.2 | 26.0 | 26.2 | 26.2 | 26.4 | 24.3 |
| o-Diaminotoluene | 31.2 | 24.8 | 20.5 | 18.8 | 17.8 | 16.4 | 8.9 |
| Conversion of o-diaminotoluene (%) | 71.5 | 77.6 | 81.5 | 83.1 | 84.0 | 85.3 | 92.2 |

TABLE 1-continued

Results of Examples 1 to 7

| Example | 1 | 2 | 3 | 4 | 5 | 6 | 7 |
|---|---|---|---|---|---|---|---|
| Yield, based on starting o-diaminotoluene (% of theory) | | | | | | | |
| Toluene | 0.4 | 0.4 | 0.5 | 0.5 | 0.4 | 0.6 | 9.2 |
| Methylcyclohexane | 0.0 | 0.0 | 0.0 | 0.0 | 0.0 | 0.0 | 0.0 |
| Methylcyclohexylamine | 0.0 | 0.0 | 0.0 | 0.0 | 0.1 | 0.1 | 0.6 |
| o-Toluidine | 11.1 | 13.4 | 16.2 | 17.4 | 18.0 | 18.9 | 20.7 |
| m-Toluidine | 35.3 | 37.8 | 38.1 | 38.5 | 38.7 | 38.8 | 37.4 |
| p-Toluidine | 24.7 | 25.9 | 26.7 | 26.8 | 26.8 | 26.9 | 24.2 |
| Total toluidines | 71.1 | 77.1 | 81.0 | 82.7 | 83.5 | 84.6 | 82.3 |
| Yield, based on reacted o-diaminotoluene (% of theory) | | | | | | | |
| o-Toluidine | 15.5 | 17.3 | 19.9 | 20.9 | 21.4 | 22.1 | 22.5 |
| m-Toluidine | 49.4 | 48.7 | 46.8 | 46.3 | 46.1 | 45.5 | 40.6 |
| p-Toluidine | 34.5 | 33.4 | 32.7 | 32.2 | 31.9 | 31.5 | 26.3 |
| Total toluidines | 99.4 | 99.4 | 99.4 | 99.4 | 99.4 | 99.1 | 89.4 |

*weight of reaction mixture at the end of the reaction time shown

As can be seen in Table 1, it was convenient to choose a reaction time of less than 6 hours under the chosen reaction conditions. Although the conversion of o-diaminotoluene could be markedly increased with a substantially longer reaction time (as demonstrated in Example 7), this was essentially only at the expense of forming by-products.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of toluidines comprising
   1) reacting
      a) 2,3-diaminotoluene, 3,4-diaminotoluene or mixtures thereof,
      with
      b) hydrogen
   in the presence of
      c) a catalyst comprising at least one iron oxide,
   wherein said reaction is carried out under elevated pressure, and at temperatures in the range of about 260° to 350° C.

2. The process of claim 1, wherein said iron oxide catalyst is selected from the group consisting of i) FeO, ii) $Fe_2O_3$, iii) $Fe_3O_4$, iv) hydrated oxides of divalent iron, v) hydrated oxides of trivalent iron, and vi) mixtures thereof.

3. The process of claim 1, wherein said iron oxide catalyst is present in an amount of 1 to 12 parts by weight, based on 100 parts by weight of diaminotoluene being reacted.

4. The process of claim 1, wherein said reaction is carried out at a hydrogen pressure of 200 to 400 bar.

* * * * *